United States Patent [19]
Winslow

[11] Patent Number: 6,063,088
[45] Date of Patent: May 16, 2000

[54] METHOD AND INSTRUMENTATION FOR IMPLANT INSERTION

[75] Inventor: Charles J. Winslow, Walnut Creek, Calif.

[73] Assignee: United States Surgical Corporation, Norwalk, Conn.

[21] Appl. No.: 08/822,530

[22] Filed: Mar. 24, 1997

[51] Int. Cl.[7] .................................................. A61B 17/56
[52] U.S. Cl. ............................... 606/61; 606/80; 606/90; 606/96; 623/17
[58] Field of Search .................................. 606/61, 60, 72, 606/73, 90, 80, 99, 96, 79; 623/17

[56] References Cited

U.S. PATENT DOCUMENTS

| | | |
|---|---|---|
| 3,486,505 | 12/1969 | Morrison . |
| 3,719,186 | 3/1973 | Merig, Jr. . |
| 3,848,601 | 11/1974 | Ma et al. . |
| 3,905,047 | 9/1975 | Long . |
| 3,916,907 | 11/1975 | Peterson . |

(List continued on next page.)

FOREIGN PATENT DOCUMENTS

| | | |
|---|---|---|
| 0307241 | 3/1989 | European Pat. Off. . |
| 0551187 | 7/1993 | European Pat. Off. . |
| 0716840 | 6/1996 | European Pat. Off. . |
| 0732093 | 9/1996 | European Pat. Off. . |
| 0734703 | 10/1996 | European Pat. Off. . |

(List continued on next page.)

OTHER PUBLICATIONS

Jose M. Otero Vich, "Anterior Cervical Interbody Fusion With Threaded Cylindrical Bone", *J. Neurosurg.*, 63:750–753, 1985.

Norman W. Hoover, "Methods of Lumbar Fusion", *The Journal of Bone and Joint Surgery*, vol. 50–A, No. 1, Jan. 1968, pp. 194–210.

Benjamin R. Wiltberger, "Intervertebral Body Fusion By the Use of Posterior Bone Dowel", pp. 69–79.

Parviz Kambin et al., "Percutaneous Lateral Discectomy of the Lumbar Spine", *Clinical Orthopaedics*, Apr. 1983, vol. 174, pp. 127–131.

Guy M. Sava et al., "Posterior Lumbar Interbody Fusion Made Simple", Neurological Surgery Associates of Cincinnati, Inc.

(List continued on next page.)

*Primary Examiner*—Guy V. Tucker
*Attorney, Agent, or Firm*—United States Surgical Corporation

[57] ABSTRACT

A system for drilling a bore in adjacent vertebrae to facilitate the insertion of a fusion implant includes a surgical retractor having a sleeve member with proximal and distal end portions and defining a longitudinal opening and a drill instrument positionable within the longitudinal opening of the surgical retractor. The retractor is configured for insertion at least partially into an intervertebral space between adjacent opposed vertebrae to distract the adjacent vertebrae to a desired predetermined distracted position. At least one anchoring member may be associated with the surgical retractor to facilitate mounting thereof to the vertebrae. The drill instrument includes an elongate member having a longitudinal passageway and defining at least one distal cutting surface and a drill member disposed within the elongate member and having a distal drill head. The drill member is rotatably movable within the elongate member and is also longitudinally fixed to the elongate member such that advancement of the drill member within the retractor causes corresponding advancement of the elongate member such that the distal cutting surface of the elongate member and the distal drill head of the drill member cooperate to cut a non-circular, e.g., an elliptical-shaped, bore in the adjacent vertebrae. Preferably, the elongate member of the drill instrument includes first and second diametrically opposed distal cutting surfaces. The cutting surfaces may be arcuately-shaped.

28 Claims, 12 Drawing Sheets

U.S. PATENT DOCUMENTS

| | | |
|---|---|---|
| 4,177,524 | 12/1979 | Grell et al. . |
| 4,484,570 | 11/1984 | Sutter et al. . |
| 4,501,269 | 2/1985 | Bagby . |
| 4,537,185 | 8/1985 | Stednitz . |
| 4,545,374 | 10/1985 | Jacobson . |
| 4,573,448 | 3/1986 | Kambin . |
| 4,677,972 | 7/1987 | Tornier . |
| 4,743,256 | 5/1988 | Brantigan . |
| 4,772,287 | 9/1988 | Ray et al. . |
| 4,820,305 | 4/1989 | Harms et al. . |
| 4,834,757 | 5/1989 | Brantigan . |
| 4,877,020 | 10/1989 | Vich . |
| 4,878,915 | 11/1989 | Brantigan . |
| 4,927,421 | 5/1990 | Goble et al. . |
| 4,936,848 | 6/1990 | Bagby . |
| 4,950,270 | 8/1990 | Bowman et al. . |
| 4,961,740 | 10/1990 | Ray et al. . |
| 5,015,247 | 5/1991 | Michelson . |
| 5,015,255 | 5/1991 | Kuslich . |
| 5,026,373 | 6/1991 | Ray et al. . |
| 5,055,104 | 10/1991 | Ray . |
| 5,059,193 | 10/1991 | Kuslich . |
| 5,062,845 | 11/1991 | Kuslich et al. . |
| 5,064,425 | 11/1991 | Branemark et al. . |
| 5,139,499 | 8/1992 | Small et al. . |
| 5,147,402 | 9/1992 | Bohler et al. . |
| 5,171,278 | 12/1992 | Pisharodi . |
| 5,192,327 | 3/1993 | Brantigan . |
| 5,195,541 | 3/1993 | Obenchain . |
| 5,263,953 | 11/1993 | Bagby . |
| 5,300,076 | 4/1994 | Leriche . |
| 5,313,962 | 5/1994 | Obenchain . |
| 5,354,302 | 10/1994 | Ko . |
| 5,357,983 | 10/1994 | Mathews . |
| 5,390,683 | 2/1995 | Pisharodi . |
| 5,395,317 | 3/1995 | Kambin . |
| 5,423,816 | 6/1995 | Lin . |
| 5,423,817 | 6/1995 | Lin . |
| 5,425,772 | 6/1995 | Brantigan . |
| 5,431,658 | 7/1995 | Moskovich . |
| 5,439,464 | 8/1995 | Shapiro . |
| 5,443,514 | 8/1995 | Steffee . |
| 5,445,639 | 8/1995 | Kuslich et al. . |
| 5,458,638 | 10/1995 | Kuslich et al. . |
| 5,484,437 | 1/1996 | Michelson . |
| 5,489,307 | 2/1996 | Kuslich et al. . |
| 5,489,308 | 2/1996 | Kuslich et al. . |
| 5,505,732 | 4/1996 | Michelson . |
| 5,522,899 | 6/1996 | Michelson . |
| 5,534,031 | 7/1996 | Matsuzaki et al. . |
| 5,554,191 | 9/1996 | Lahille et al. . |
| 5,562,736 | 10/1996 | Ray et al. . |
| 5,571,109 | 11/1996 | Bertagnoli . |
| 5,571,189 | 11/1996 | Kuslich . |
| 5,571,192 | 11/1996 | Schönhöffer . |

FOREIGN PATENT DOCUMENTS

| | | |
|---|---|---|
| 2295729 | 12/1974 | France . |
| 2350824 | 3/1977 | France . |
| 2710519 | 9/1993 | France . |
| 1961531 | 12/1969 | Germany . |
| 3505567 | 2/1985 | Germany . |
| 4302397 | 1/1993 | Germany . |
| 4323595 | 7/1993 | Germany . |
| 57-29348 | 2/1982 | Japan . |
| 58-78653 | 5/1983 | Japan . |
| 61-135652 | 6/1986 | Japan . |
| 62-164458 | 7/1987 | Japan . |
| 63-43654 | 2/1988 | Japan . |
| 1502402 | 8/1989 | Japan . |
| 1314560 | 12/1989 | Japan . |
| 8707827 | 12/1987 | WIPO . |
| 8912431 | 12/1989 | WIPO . |
| 91066261 | 5/1991 | WIPO . |
| 9417759 | 8/1994 | WIPO . |
| 9608205 | 3/1996 | WIPO . |

OTHER PUBLICATIONS

CAGE CH: Lumbar Spacing Cages, *Scientix*.

Actualites Vertebrales, La Herni Discale Cervicale, No. 2, Avril 1994, pp. 1–11.

Kiyoshi Kaneda and Isao Yamamoto, "Spinal Instumentation Surgery In Lumbar and Lumbosacral Spine, " *The Improvement of Medicine*, vol. 147, No. 14, Dec. 31, 1988.

Hiroshi Yamamoto, "Spinal Instrumentation For Lumbar Spine Segmental Transverse Wiring For Spondylolysis and Pedicular Screw–Spinal Plate For Spondylolisthesis," *The Improvement of Medicine*, vol. 145, No. 1, Apr. 2, 1988.

Kenichiro Shibata, Masayoshi Oga, Kazuo Hayashi, Yoichi Sugioka, "A New Contrivance of Anterior Spinal Fusion in Cervical Spine", *Orthopaedic and Traumatic Surgery*, vol. 35, No. 3, pp. 811–813, 1987.

Haruo Tsuji, "Anterior Body Fusion of Lumbar Spine Hernia, " *Operation*, vol. 41, No. 11, pp. 1803–1811, 1987.

Hirotugu Oda, Shinya Kawai, Tetsuro Murakami, et al., "Osteoplastic Hemi/Bilateral Partial Laminectomy of Lumbar Spinal Hernia," *Operation*, vol. 41, No. 11, pp. 1785–1791, 1987.

Teiji Yano, et al., "Treatment of Spondylolisthesis By Posterior Fusion With Bone Grafting To Neutral Arch Defect," *Clinical Orthopaedic Surgery*, vol. 17, No. 4, pp. 394–399, 1982.

Toshihiko Yamane, et al., "A Case Report of Multiple Lumbar Spondylolyses With Spondylolisthesis," *Clinical Orthopaedic Surgery,* vol. 23, No. 3, pp. 311–314, 1988.

M. Maeshiro, K. Otani, K. Shibasaki, S. Nakai, K. Nemoto, M. Yoshida, "Posterior Fracture–Dislocation of the Thoracic Spine; Two Case Report," *Orthopedic Surgery*, vol. 39, No. 9, pp. 1373–1377, 1988–9.

Kunio Takaoka, "Clinical Application of Ceramic Implants in Orthopedics Surgery," *Medicine Philosophics*, vol. 4, No. 7, pp. 546–552, 1985.

Y. Yamano, Y. Mikawa, R. Watanabe, et al., "Anterior Body Fusion of Lumbar Degenerative Spondylolisthesis," *Journal of the Western Japanese Research Society For Spine*, vol. 13, pp. 46–50.

Dual Chisel and Its Bank Bones (Skimud Subkortikale Bones) For Posterior Lumbar Interbody Fusion—In Order To Simplify and Regularize the Surgical Procedure, *Orthopaedic Surgery*, vol. 11, pp. 150–153.

Vertebral Body Distraction System (Caspar), "*Orthopaedic Surgery*", vol. 11, pp. 135–139.

Takayoshi Ueda, et al., "Instrumentation Surgery of Lumbar Interbody Fusion," *Central Japan Journal of Orthopaedic& Traumatic Surgery*, pp. 87–89.

Haruo Tsuji, et al., "Development and Clinical Application of Artificial Intervertebral Disc For Cervical Disc Lesions," *Central Japan Journal of Orthopaedic& Traumatic Surgery*, pp. 1505–1506.

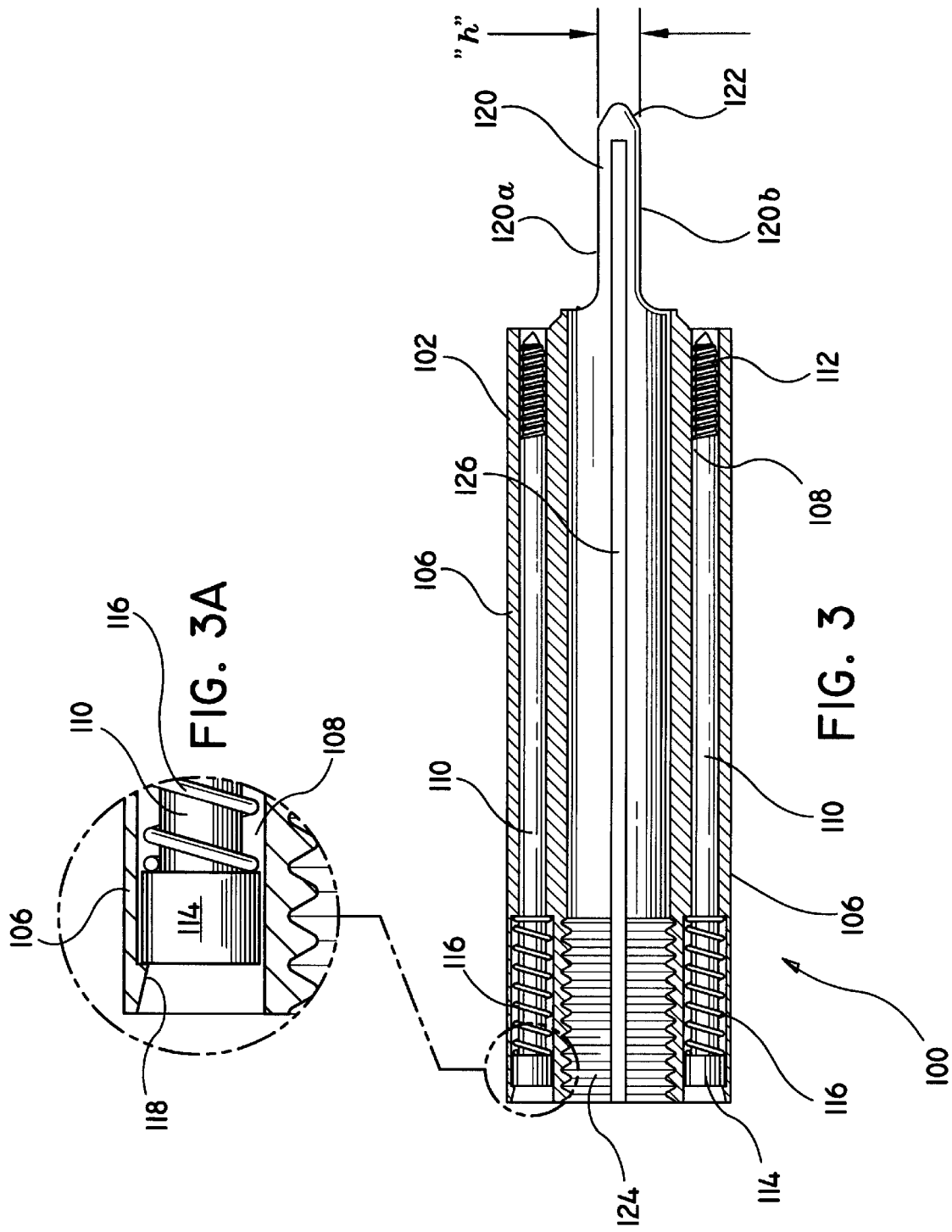

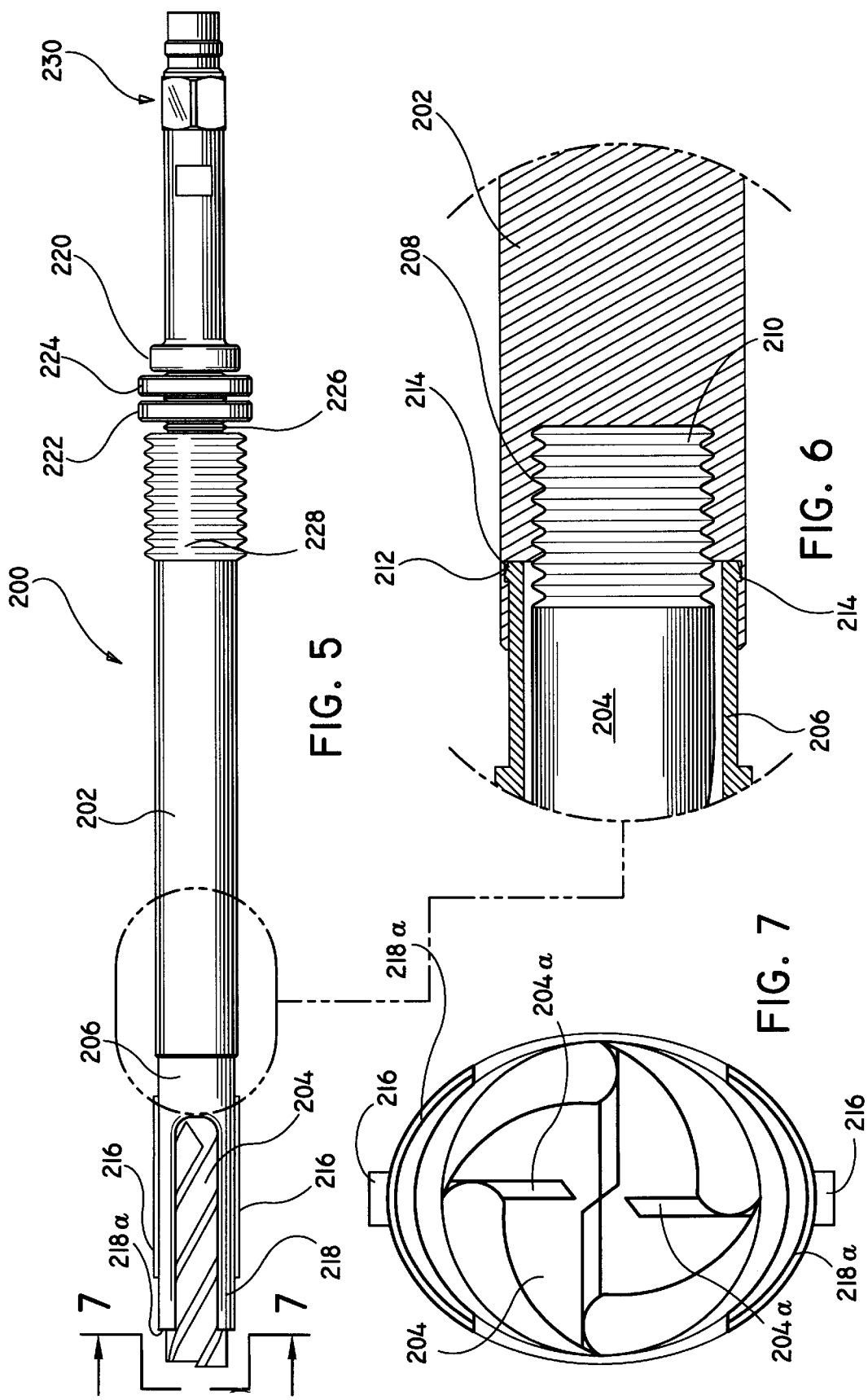

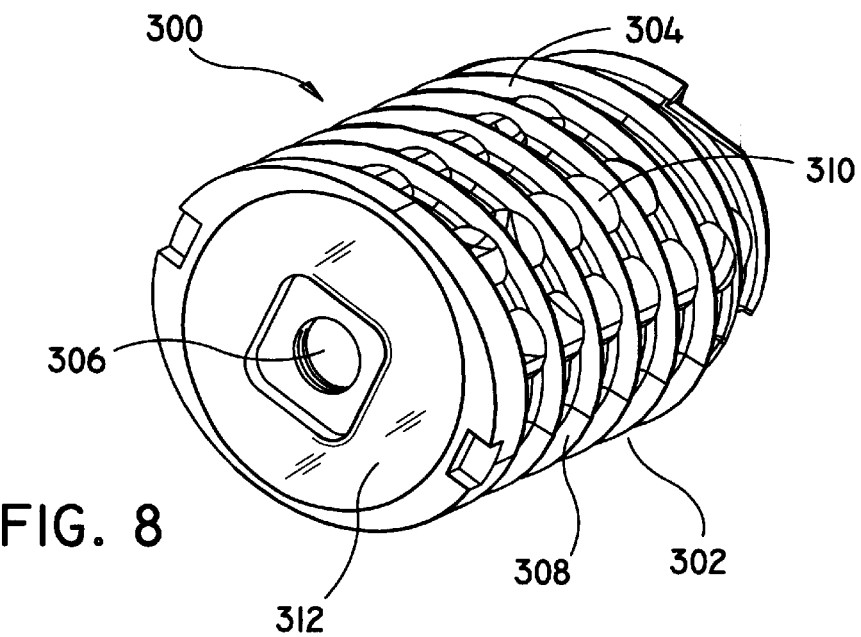
FIG. 8
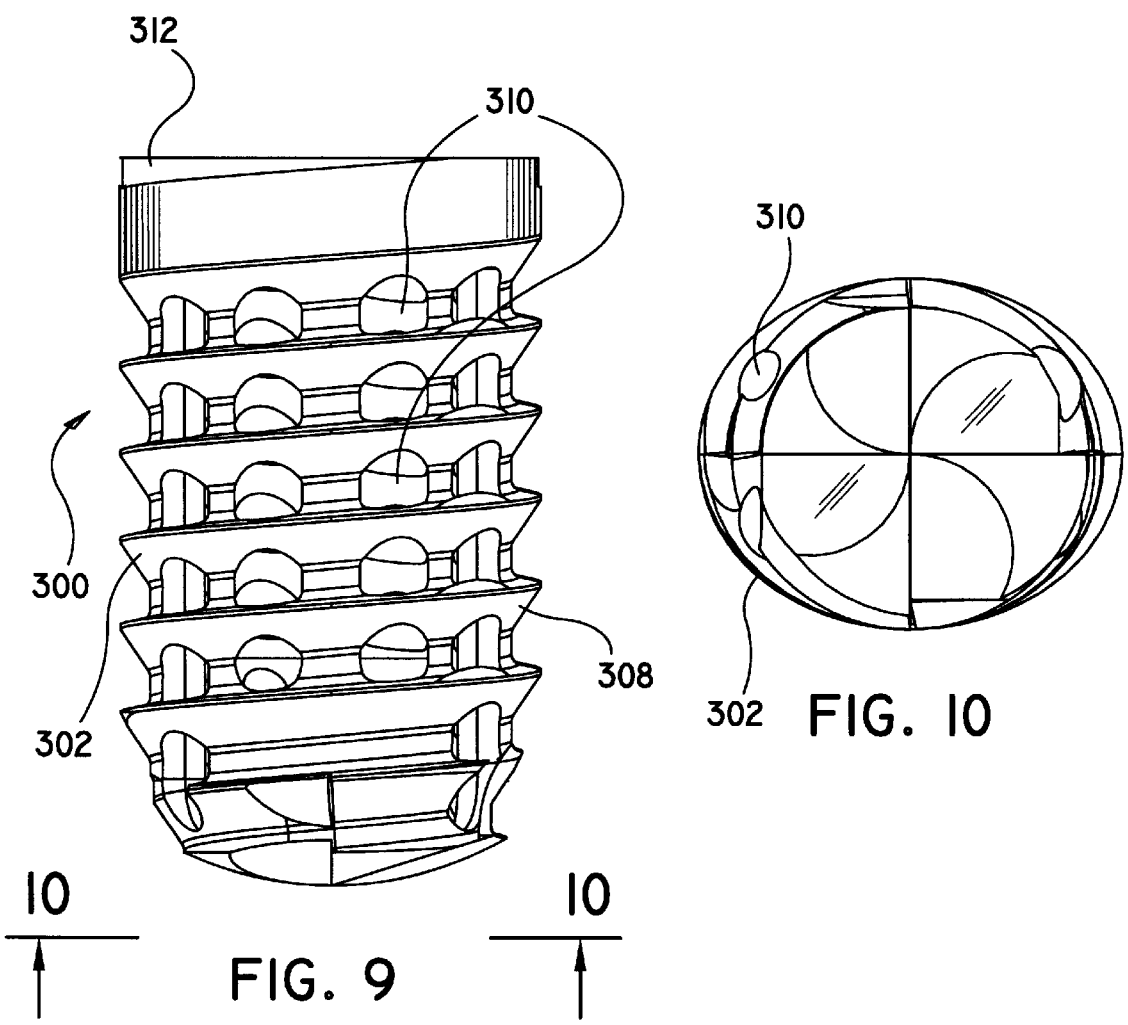
FIG. 9
FIG. 10

METHOD AND INSTRUMENTATION FOR IMPLANT INSERTION

BACKGROUND

1. Technical Field

The present disclosure generally relates to a method and associated instrumentation for implant insertion and, in particular, to a method and instrumentation for insertion of spinal implants to facilitate fusion of adjacent vertebral bodies.

2. Background of the Related Art

A large number of orthopedic procedures involve the insertion of either natural or prosthetic implants into bone or associated tissues. These procedures include, for example, ligament repair, joint repair or replacement, non-union fractures, facial reconstruction, spinal stabilization and spinal fusion. In a typical procedure, an insert, dowel or screw is inserted into a prepared bore formed in the bone or tissues to facilitate repair and healing. See, for example, U.S. Pat. No. 5,470,334 to Ross et al.; U.S. Pat. No. 5,454,811 to Huebner; U.S. Pat. No. 5,480,403 to Lee et al.; U.S. Pat. No. 5,358,511 to Gatturna et al.; and U.S. Pat. No. 4,877,020 to Vich.

Some implants are particularly configured with cavities and bores to facilitate bony ingrowth and enhance anchoring of the implant at the insertion site. See, for example, U.S. Pat. No. 4,328,593 to Sutter et al.; U.S. Pat. No. 4,936,851 to Fox et al.; and U.S. Pat. No. 4,878,915 to Brantigan. Other specialized implants include fusion cages having internal cavities to receive bone growth stimulation materials such as bone chips and fragments. See, for example, U.S. Patent No. 4,501,269 to Bagby; U.S. Pat. No. 4,961,740 to Ray et al.; U.S. Pat. No. 5,015,247 to Michaelson; and U.S. Pat. No. 5,489,307 to Kuslich et al. These types of implants are particularly well suited for intervertebral spinal fusion procedures necessitated by injury, disease or some degenerative disorder of the spinal disc. Subsequently, there may be progressive degeneration leading to mechanical instability between adjacent vertebrae necessitating direct fusion of the vertebrae while maintaining a pre-defined intervertebral space. This fusion may be accomplished by the insertion of one or more of the specialized implants as discussed above and also discussed in commonly assigned U.S. Pat. No. 5,026,373, the contents of which are incorporated herein by reference.

Both anterior (transabdominal) and posterior surgical approaches are used for interbody fusions of the lumbar spine. Fusions in the cervical area of the spine are also performed using an anterior or a posterior approach. Typically, an implant such as a plug, dowel, prosthesis or cage is inserted into a preformed cavity inside the interbody, interdiscal space. Since it is desirable in these procedures to promote a "bone to bone" bridge, connective tissue and at least a portion of the distal tissue is removed. Preferably, relatively deep cuts are made in the adjacent bones in order to penetrate into the softer, more vascularized cancerous region to facilitate bone growth across the implant.

One of the more critical tasks performed in the insertion of a surgical fusion implant, particularly, in intervertebral spinal fusion, is the formation of the implant receiving cavity or bore within the adjacent vertebrae. More particularly, the drilled bore should be centered with respect to and preferably parallel to the vertebral end plates to ensure removal of equal portions of bone from the adjacent vertebrae throughout the length of the cut and subsequent appropriate seating of the implant relative to the vertebral bodies.

Surgical instruments for spinal fusion implant insertion are known. For example, U.S. Pat. No. 5,484,437 to Michelson discloses a method and apparatus incorporating an outer and an inner sleeve arrangement. The outer sleeve has teeth at one end which are driven directly into the posterior surface of the adjacent vertebrae. The inner sleeve is positioned within the outer sleeve and serves to guide instruments such as a drill used to form the implant receiving bore. U.S. Pat. No. 5,487,307 to Kuslich et al.; U.S. Pat. No. 5,015,247 to Michelson; and U.S. Pat. No. 4,878,915 to Brantigan disclose similar arrangements. Other arrangements include the use of guide rods which are placed in pilot holes formed in the vertebral bodies. The guide rods guide a bore forming hollow drill into the intervertebral space.

Although some of the current instrumentation and methods associated therewith for enhancing the placement of spinal fusion implants have been generally effective for their intended purposes, there exists certain limitations with the design of this instrumentation which detract from their usefulness. For example, the arrangement disclosed in the Michelson '437 patent and similar arrangements do not provide for automatic alignment of the outer sleeve to ensure that the bore formed by a drill introduced into the outer sleeve is in optimal alignment for a tapping procedure (if required) and reception of the spinal implant Rather, such orientation is dependent directly upon the skill of the surgeon. Moreover, the outer sleeve, which is only mounted only at its extreme distal end to the posterior surface of the adjacent vertebrae, is subject to disorientation or dislodgment during insertion and/or removal of the drill and/or tapping instrument. Similarly, the use of guide rods increases the number of steps required to implant the fusion cage and is also subject to possible misalignment.

U.S. patent application Ser. No. 08/615,379, filed Mar. 14, 1996, the contents of which are incorporated herein by reference, discloses a method and associated instrumentation to facilitate the introduction of a fusion implant. The instrumentation disclosed in the '379 application ensures optimal alignment of the drilled bore for reception of the fusion implant and, if appropriate, for bore tapping procedures. The instrumentation includes a surgical retractor and a drill. The retractor is configured for distracting adjacent vertebral bodies to facilitate the insertion and application of an implant, for providing a cannula for insertion of auxiliary instruments, e.g., the drill, and for ensuring proper alignment of the instrumentation and accurate insertion of the implant. The instrumentation and method disclosed in the '379 application is well suited for implanting an implant having a general circular cross-sectional portion such as the aforedescribed Ray '373 fusion cage.

Commonly assigned U.S. patent application Ser. No. 08/734,911, filed Oct. 22, 1996, the contents of which are incorporated herein by reference, discloses an implant member configured for insertion within a space defined between adjacent bone structure and having a longitudinal portion with a generally elliptical transverse cross-sectional dimension. The elliptical configuration of the implant provides an enhanced level of contact and support of the bone structures, e.g., adjacent vertebrae, when implanted.

SUMMARY

Accordingly, the present disclosure is directed to a system and associated method to facilitate insertion of fusion implants, e.g. non-circular implants such as the elliptical implant disclosed in the '911 application. In a preferred embodiment, a system for drilling a bore in adjacent vertebrae to facilitate the insertion of a fusion implant is provided, The system includes a surgical retractor including a sleeve member with proximal and distal end portions and defining a longitudinal opening and a drill instrument positionable within the longitudinal opening of the surgical retractor. The distal end portion of the retractor is configured for insertion at least partially into an intervertebral space between adjacent opposed vertebrae to distract the adjacent vertebrae to a desired predetermined distracted position.

Preferably, the drill instrument includes an elongate member having a longitudinal passageway and defining at least one distal cutting surface and a drill member disposed within the elongate member and having a distal drill head. The drill member is rotatably movable within the elongate member and is also longitudinally fixed to the elongate member such that advancement of the drill member within the retractor causes corresponding advancement of the elongate member such that the distal cutting surface of the elongate member and the distal drill head of the drill member cooperate to cut a bore, e.g., an elliptical-shaped bore, in the adjacent vertebrae. Preferably, the elongate member of the drill instrument includes first and second diametrically opposed distal cutting surfaces. The cutting surfaces may be arcuately-shaped.

Preferably, the distal end portion of the retractor includes two spaced apart retractor arms having first and second support surfaces which respectively engage and distract upper and lower vertebrae. At least one anchoring member may be associated with the surgical retractor to facilitate mounting of the retractor to the vertebrae.

The system may further include alignment means for aligning and maintaining the elongate member of the drill instrument at a predetermined angular orientation within the sleeve member of the surgical retractor. The preferred alignment means is adapted to angularly orient the first and second distal cutting surfaces in general alignment within respective retractor arms of the surgical retractor. The alignment means may include at least one groove defined in the sleeve member of the surgical retractor, the one groove dimensioned to accommodate a corresponding spline of the elongate member.

The present disclosure is also directed to a system for drilling a bore in adjacent vertebrae to facilitate the insertion of a fusion implant comprising a surgical retractor including a sleeve member having proximal and distal end portions and defining a longitudinal opening, with the distal end portion configured for insertion at least partially into an intervertebral space between adjacent opposed vertebrae to distract the adjacent vertebrae and the sleeve member including an internal threaded portion. A drill instrument is positionable within the longitudinal opening of the surgical retractor, and includes a drill member having a distal cutting head and an external threaded portion engageable with the internal threaded portion of the retractor whereby rotation of the drill instrument causes distal translation of the drill instrument relative to the surgical retractor.

A method for performing a surgical procedure with the system is also disclosed. The method includes the steps of providing a surgical retractor including an elongate member defining a longitudinal opening and having two spaced apart retractor arms with first and second supporting surfaces at its distal end, inserting the retractor arms of the retractor within the intervertebral space whereby the first and second supporting surfaces of each retractor arm respectively engage and distract the adjacent opposed vertebras, mounting the surgical retractor to the adjacent vertebrae by securing an anchor member associated with the surgical retractor to the adjacent vertebrae and performing the surgical procedure adjacent the distracted vertebrae by, e.g., introducing surgical instrumentation within the opening of the surgical retractor.

A method for fusing adjacent vertebral bodies with the system is also disclosed. The method includes the steps of accessing the intervertebral disc space, providing a retractor including a retractor sleeve having opposed retractor arms extending in a general longitudinal direction, positioning the retractor arms within the intervertebral disc space whereby first and second supporting surfaces of each arm contact opposed vertebra bodies, introducing a drill instrument into the retractor sleeve and advancing the drill instrument within the sleeve to the disc space wherein the drill instrument includes an elongate member having a longitudinal passageway and defming at least one distal cutting surface and a drill member rotatably mounted within the elongate member and having a distal cutting head, actuating the drill instrument such that the distal cutting head of the drill member and the distal cutting surface of the elongate member are advanced into the adjacent vertebrae to cooperate and cut a bore in the adjacent vertebra, removing the drill instrument from the sleeve, and introducing a fusion implant into the bore. Preferably an elliptical bore is formed and a fusion implant having an elliptical cross-sectional dimension is inserted into the bore.

BRIEF DESCRIPTION OF THE DRAWINGS

Preferred embodiments of the disclosure are described herein with reference to the drawings wherein:

FIG. 1A is a perspective view of an insertion instrument and detached T-handle utilized in inserting an implant within the adjacent bony structures;

FIG. 3 is a side view in cross-section of the surgical retractor of FIG. 2;

FIG. 3A is an isolated view of the anchoring member being retained within the retractor, FIG. 5 is a side plan view of the drilling instrument;

FIG. 6 is an isolated view in cross-section illustrating the mounting of the drill shaft and drill bit and the mounting of the extension sleeve and the drill shaft;

FIG. 7 is an axial view of the drilling instrument;

FIG. 8 is a perspective view of the implant having an elliptical cross-section to be inserted into the bore of the bony structures;

FIG. 9 is a side plan view of the implant of FIG. 8;

FIG. 10 is a cross-sectional view of the implant taken along the lines 10—10 of FIG. 9;

FIG. 16A is a cross-sectional view taken along the lines 16A—16A of FIG. 16;

DETAILED DESCRIPTION OF THE PREFERRED EMBODIMENTS

The preferred embodiments of the method and instrumentation disclosed herein are discussed in terms of orthopedic spinal fusion procedures and instrumentation. It is also envisioned, however, that the disclosure is applicable to a wide variety of procedures including, but, not limited to ligament repair, joint repair or replacement, non-union fractures, facial reconstruction and spinal stabilization. In addition, it is believed that the present method and instrumentation finds application in both open and minimally invasive procedures including endoscopic and arthroscopic procedures wherein access to the surgical site is achieved through a cannula or small incision.

The following discussion will include a description of each instrument utilized in performing a spinal fusion method followed by a description of the preferred method for spinal fusion utilizing the instrumentation in accordance with the present disclosure.

In the discussion which follows, the term "proximal", as is traditional, will refer to the portion of the structure which is closer to the operator, while the term "distal" will refer to the portion which is further from the operator.

Figure 1:
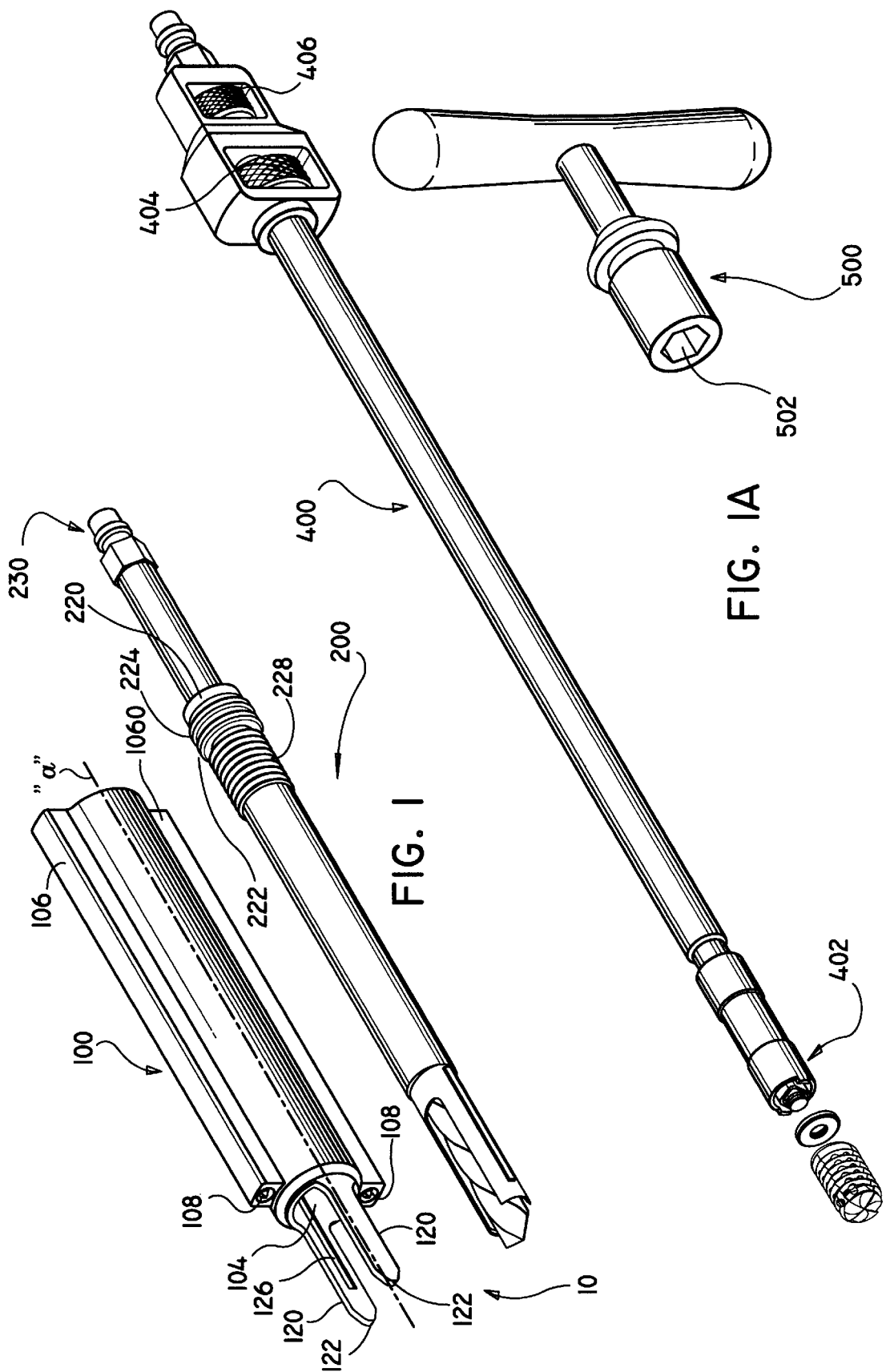
FIG. 1 is a perspective view of the surgical retractor utilized in distracting adjacent bony structures and the surgical drilling instrument utilized in drilling a bore within the adjacent bony structure in accordance with the principles of the present disclosure.

Referring now to the drawings in which like reference numerals identify similar or identical elements through the several views, FIG. 1 illustrates, in perspective, the surgical system in accordance with the principles of the present disclosure. System 10 is particularly contemplated for facilitating the insertion of a fusion implant within the intervertebral space defined between adjacent vertebrae, and, more particularly, in the insertion of the fusion implant disclosed in the aforementioned '911 application, which has a longitudinal portion with a generally elliptical cross-section. This implant will be discussed in greater detail hereinbelow. System 10 generally includes two surgical instruments, namely retractor 100 and drilling instrument 200 which is positionable within the retractor 100.

Figure 2:
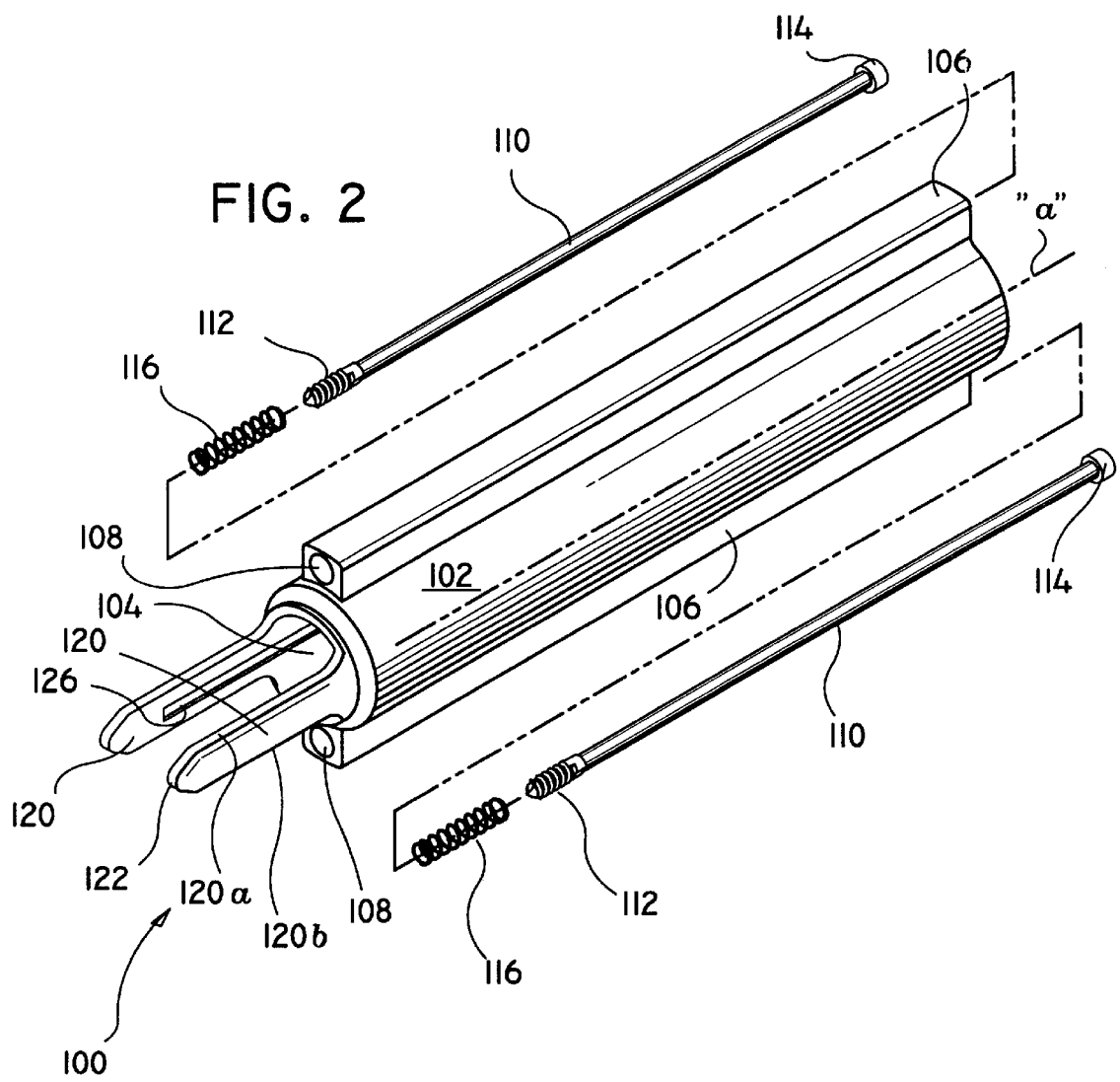
FIG. 2 is a perspective view with parts separated of the surgical retractor of FIG. 1.
Figure 4:
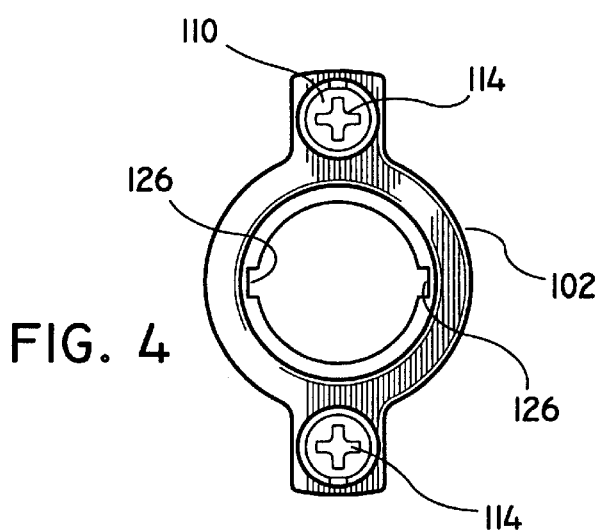
FIG. 4 is an axial view of the surgical retractor.

With reference now to FIGS. 2–4, in conjunction with FIG. 1, retractor 100 includes elongated retractor sleeve 102 defining a longitudinal axis "a" and having longitudinal opening or passageway 104 extending therethrough. Retractor sleeve 102 includes first and second diametrically opposed rails 106 extending longitudinally along the outer surface of the retractor sleeve 102. Each rail 106 has a longitudinal opening 108. An anchoring member 110 is disposed within opening 108 of each rail 106. Anchoring member 110 is intended to positively fix retractor 100 to the bony structures, e.g, adjacent vertebrae. In the preferred embodiment, anchoring member 110 is in the form of an elongated screw as shown and includes a distal screw thread 112 which is advantageously configured to penetrate and become mounted within bony tissue. The proximal end of anchoring member 110 includes structure, e.g., a Phillips head 114, to be engaged by a driving member, e.g., a Phillips head screw driver or the like, to rotate and advance the anchoring member 110 in a conventional manner. As depicted in FIG. 3, each anchoring member 110 is biased proximally by coil spring 116 whereby distal screw thread 112 is disposed within opening 106 of rail 106 in the unadvanced position of the anchoring member 110. Anchoring member 110 is retained within each rail 106 by lip 118 extending within opening 108 of each rail 106 and engaging the proximal edge of the anchoring member (FIG. 3A), thereby preventing the anchoring member 110 from exiting the proximal end of retractor sleeve 102.

Anchoring member 110 thus constitutes "anchoring means" to positively mount surgical retractor 100 to the adjacent vertebrae. Other forms of anchoring means are envisioned as well such as, but, not limited to, fasteners, staples, clips etc . . . which may be driven from the proximal location of retractor sleeve 102. Additional forms of "anchoring means" may include suture ties, bands, clamps, etc.

With reference again to FIGS. 2–4, retractor 100 includes first and second diametrically opposed retractor arms 120 extending from the distal end of retractor sleeve 102. Each retractor arm 120 has first and second supporting surfaces 120a, 120b (FIG. 3) extending in general parallel relation to each other and preferably to the longitudinal axis of retractor sleeve 102. The height "h" of each arm (i.e., the distance between supporting surfaces 120a, 120b) corresponds to the height of the space between adjacent bony structures to be distracted. For example, in spinal implant application, the height "h" of each arm can range from about 0.28 inches to about 0.35 inches. Each arm 120 further includes tapered end portions 122 defining a general V-shaped configuration. End portions 122 facilitate insertion of retractor arms 120 within the surgical site, e.g., within the intervertebral space.

The proximal end of retractor sleeve 102 defines an inner threaded bore 124. Threaded bore 124 assists in causing translation of the surgical drilling instrument 200 through retractor sleeve 102 as will be discussed. Retractor 100 further includes first and second inner longitudinal recesses 126 which each extend from the proximal end of retractor sleeve 102 to an intermediate point of retractor arms 120. First and second longitudinal recesses 126 function in maintaining proper alignment of the surgical drilling instrument 200 inserted within retractor 100 as will be appreciated from the description provided hereinbelow.

Referring now to FIGS. 5–7, in conjunction with FIG. 1, the surgical drilling instrument 200 of the system 10 will be discussed. Drilling instrument 200 is advantageously configured to form an elliptical-shaped bore in the adjacent vertebrae to accommodate the elliptical implant. Clearly, the drill can be configured to form other shaped bores. Drilling instrument 200 includes drill shaft 202, drill bit 204 connected to and extending distally from the drill shaft 202 and extension sleeve 206 mounted to the distal end of the drill shaft 202. In a preferred arrangement, depicted in detail in FIG. 6, drill shaft 202 includes an internal threaded recess 208 which threadably engages external threaded portion 210 of drill bit 204 to connect the components. With this arrangement, rotational movement of the drill shaft 202 causes corresponding rotational movement of the drill bit 204. Drill bit 204 defines distal cutting edges 204a which form a generally circular bore in the bone structures.

Extension sleeve 206 is mounted to drill shaft 202 to permit relative rotational movement of the two components. In a preferred arrangement, drill shaft 202 includes a circumferential mounting recess 212 which receives correspondingly dimensioned circumferential mounting lip 214 of extension sleeve 206 in sliding manner to permit rotational movement of the drill shaft 202 and, thus, rotational movement of the drill bit 204 within the extension sleeve 206. Extension sleeve 206 further defines first and second axial splines 216 disposed on the outer surface of the extension sleeve 206 in diametrical arrangement. Axial splines 216 are received within longitudinal recesses 126 (FIG. 2) within the interior of the sleeve 206 to rotationally fix the extension sleeve 206 within retractor 100.

Extension sleeve 206 further defines diametrically opposed cutting arms 218 at its distal end. Cutting arms 218 define distal cutting surfaces 218a which are advantageously dimensioned to cut or shear bony tissue upon advancement of the drill instrument 200 into the tissue. Cutting surfaces 218a are preferably arcuate in cross-section as best depicted in FIG. 7. As will be better appreciated hereinbelow, cutting surfaces 218a in combination with drill bit 202 form a general elliptical bore in the bony tissue. In particular, drill bit 202 forms through a drilling action a circular hole while cutting surfaces 218a cut by a chiseling, shearing action diametrically opposed arcuate sections adjacent the circular bore thereby defining an elliptical configuration of the formed bore in the tissue section.

Referring still to FIGS. 5–7, drill shaft 202 further includes stationary collar 220 and first and second movable collars 222, 224 adjacent the stationary collar 220. Moveable collars 222, 224 are threadably mounted on threaded portion 226 and are each moveable on the threaded portion 226 between a proximalmost position adjacent stationery collar 220 and a distalmost portion remote from the collar 220. First collar 222 serves as a positioning collar, i.e., by adjusting the positioning of first collar 222 on threaded portion 226, the depth of penetration of drill shaft 202 into the bony structures may be adjusted. Second collar 224 serves as a locking collar to selectively lock the first collar 222 at a predetermined location on threaded portion 226.

Drill shaft 202 further includes an intermediate external threaded portion 228 disposed at about the midpoint of the drill shaft 202 to assist in translation of the drill shaft 202 within the retractor 100. More particularly, threaded portion 228 cooperatively threadably engages internal threaded bore 124 disposed within retractor sleeve 102. Accordingly, rotation of the drill shaft 202 causes the drill shaft 202 to translate longitudinally within the retractor 100. The proximal end of drill shaft 202 includes mounting structure 230, e.g., a hexagonal-shaped head, which cooperates with corresponding structure of a T-shaped handle (to be discussed) to assist in operating the drilling instrument.

Referring now to FIGS. 8–10, the spinal implant 300 to be utilized with the surgical system of the present invention is illustrated. Spinal implant 300 is disclosed in the aforementioned U.S. application Ser. No. 734,911. The implant 300 is contemplated to be self-tapping, i.e., the implant is intended to be inserted within a preformed bore in adjacent bone structures, e.g., adjacent vertebrae, without necessitating tapping of an internal thread within the bone structure prior to insertion. Implant 300 includes an implant body 302 which is generally elliptical in cross-section along at least a portion of its length. This configuration provides a greater surface area of the implant so as to facilitate contacting engagement and support of the implant with the adjacent vertebrae. As described below, the implant in the inserted position is oriented so that the major diameter is in the transverse direction and the minor diameter is in the superior-inferior direction. Implant body 302 includes an outer wall 304 which encloses internal cavity 306. An external threaded configuration 308 is disposed on the outer wall 304 to assist in advancing the implant body 302 within the preformed bore. Internal cavity 306 accommodates bone growth including substances which facilitate the fusion process. The threaded configuration is preferably a self-tapping thread. A plurality of apertures 310 extend through outer wall 304 of implant body 302 in communication with the internal cavity 306. Apertures 310 are preferably formed by broaching grooves in the internal surface of the internal cavity. The effect of such broaching is to remove material from the valleys between the threads, thus defining the apertures 310. The advantages of such an arrangement are disclosed in U.S. Pat. No. 4,961,740, the contents of which are incorporated herein by reference, and include immediate bone to bone contact between the vertebral bodies or bone structures and the bone inducing substances packed within the internal cavity 306 of the implant body 302 upon its insertion. Apertures 310 are preferably substantially the same in dimension although it is envisioned that the dimensions of the apertures may vary to provide for more or less bone to bone contact as desired. The implant 300 further includes an end cap 312 mountable to one end of the cage body 302 to enclose the internal cavity 306. The end cap 312 preferably includes an external threaded portion which threadably engages an internal threaded portion of implant body 302.

FIG. 1A illustrates one type of insertion instrument 400 utilized to insert the implant 300 within the intervertebral space and a T-shaped handle 500 utilized to actuate the insertion instrument 400 and the drilling instrument 200. Insertion instrument 400 is disclosed in commonly assigned U.S. patent application Ser. No. 08/616,120, filed Mar. 14, 1996, the contents of which are incorporated herein by reference. Insertion instrument 400 includes implant engaging structure 402 at its distal end which is correspondingly configured to mount and release implant 300 as will be discussed hereinbelow. A pair of control wheels 404, 406 serve to control actuation of insertion instrument 400 thereby controlling mounting and releasing of the implant within the intervertebral space. T-shaped handle 500 is mountable to the proximal end of drilling instrument 200 and to the proximal end of the insertion instrument 400. Handle 500 includes hex-head recess 502. Further details of this instrument 400 and handle 500 implant may be ascertained by reference to the '120 application.

Use of the System For Insertion of the Fusion Implant

The use of the system 10 for the insertion of the fusion implant 300 into an intervertebral space defined between adjacent lumbar vertebrae will now be described. The subsequent description will be particularly discussed in conjunction with an open anterolateral approach for spinal fusion implant insertion. However, it is to be appreciated that other approaches, e.g., posterior, direct anterior, etc . . . could be utilized. Laparoscopic approaches are also envisioned.

Figures 11, 12:
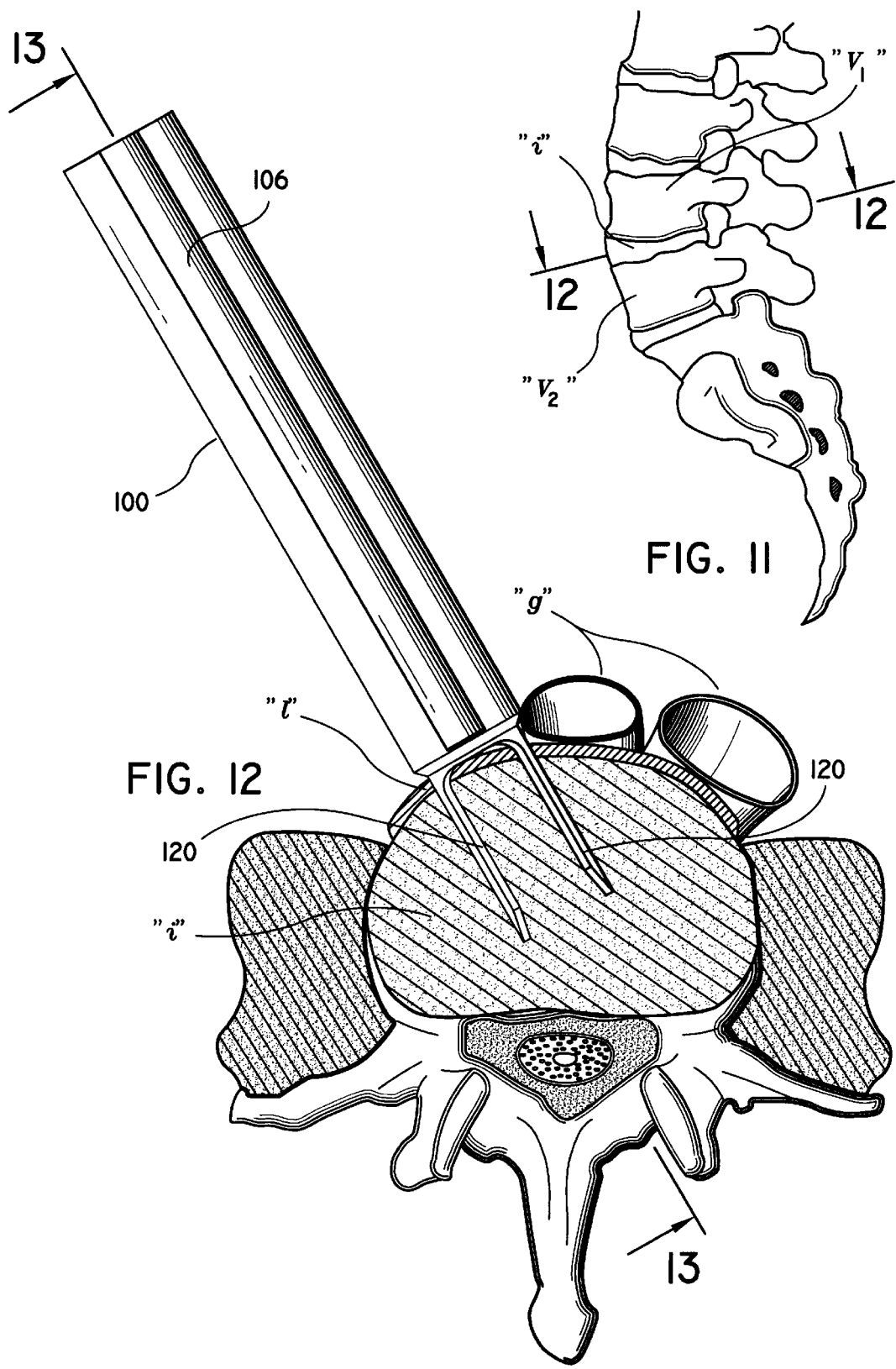
FIG. 11 is a view of a portion of the vertebral column.
FIG. 12 is a sectional view of the vertebral column taking along the lines 12—12 of FIG. 11 illustrating insertion of the surgical retractor within the intervertebral space.

With respect now to FIGS. 11–12, the desired intervertebral space "i" between adjacent vertebrae "$v_1$, $v_2$" is accessed utilizing appropriate retractors to expose the anterior vertebral surface. Thereafter, retractor 100 is inserted within the intervertebral space "i" from an antero-lateral or oblique approach with relation to the vertebral columns "$v_1$, $v_2$" as depicted in FIG. 12. Such approach provides advantages with regard to avoiding interference by the great vessels "g", limiting penetration of the anterior longitudinal ligament "l" and minimizing resection of the psoas muscle. The retractor 100 may be inserted by impacting the proximal end of the retractor to drive the retractor into the intervertebral space.

Figure 13:
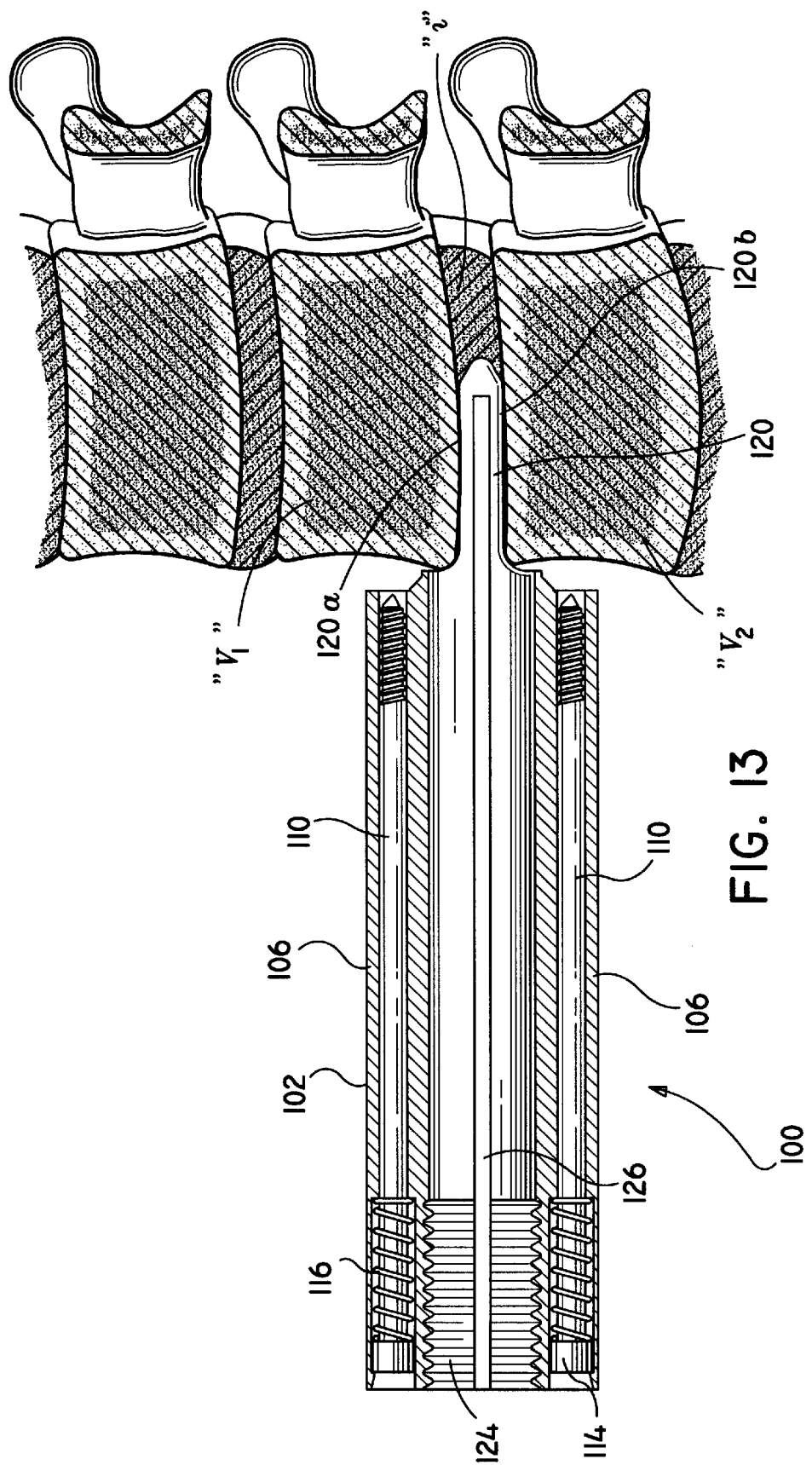
FIG. 13 is a cross-sectional view further illustrating the surgical retractor inserted within the intervertebral space.
Figure 14:
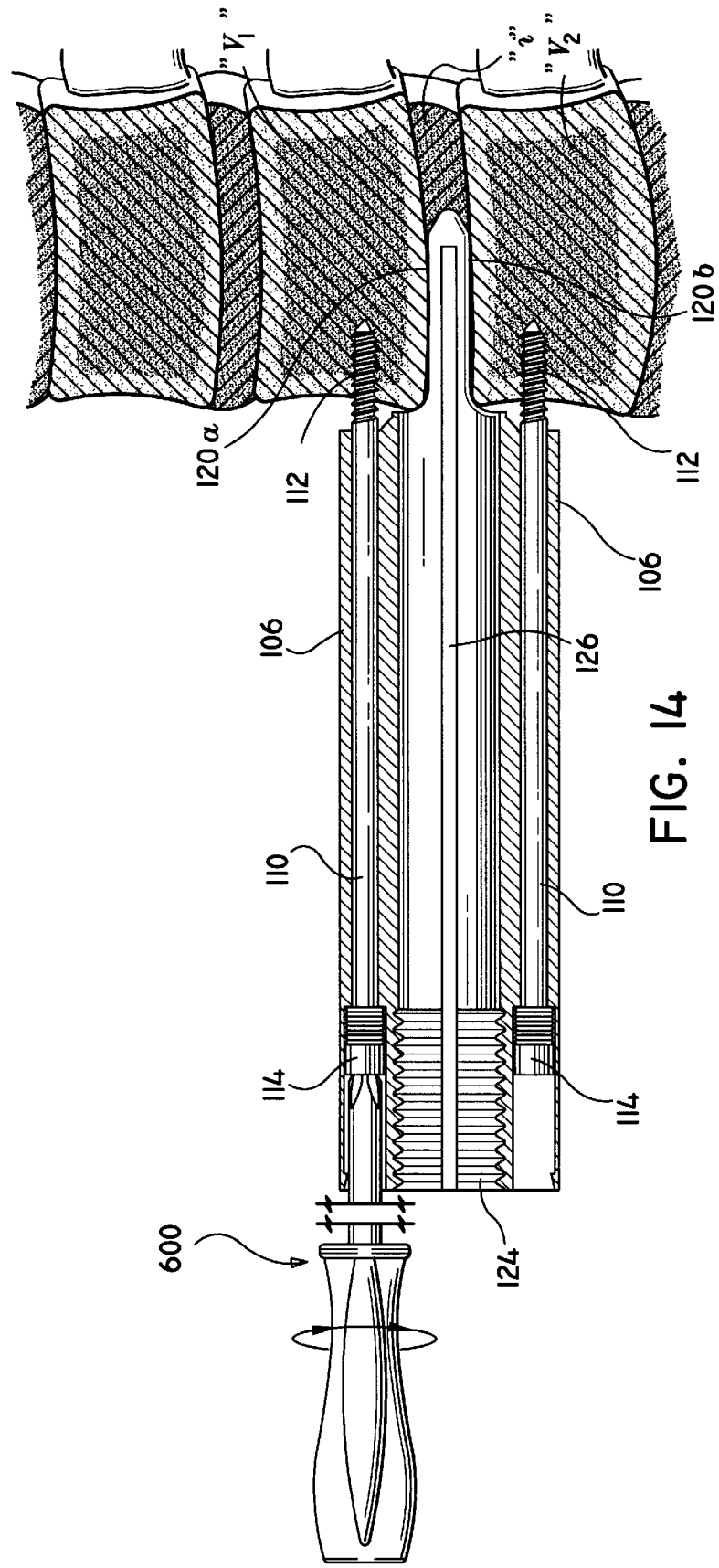
FIG. 14 is a view similar to the view of FIG. 13 illustrating mounting of the anchoring screws into the vertebral column.

FIG. 13 depicts retractor 100 positioned within the intervertebral space "i" with the retractor arms 120 arranged such that the first and second supporting surfaces 120a, 120b of each retractor arm 120 respectively engage the opposed vertebral bodies "$v_1$, $v_2$". Upon insertion of retractor arms 120, the vertebral bodies "$v_1$, $v_2$" are distracted whereby the retractor arms 120 become firmly lodged within the intervertebral space "i". As noted above, upon insertion of the retractor arms 120, the vertebrae "$v_1$,$v_2$" are distracted to a desired operative position. As depicted in FIG. 14, anchoring members 110 are then advanced within their respective openings 108 of rails 106 and mounted within the vertebra "$v_1$, $v_2$" with the use of mounting tool 600, e.g., an elongated driver or the like, whereby the distal screw thread 112 of each anchoring member engages the vertebral tissue. As a result, retractor 100 is positively fixed to the vertebral column.

Figure 15:
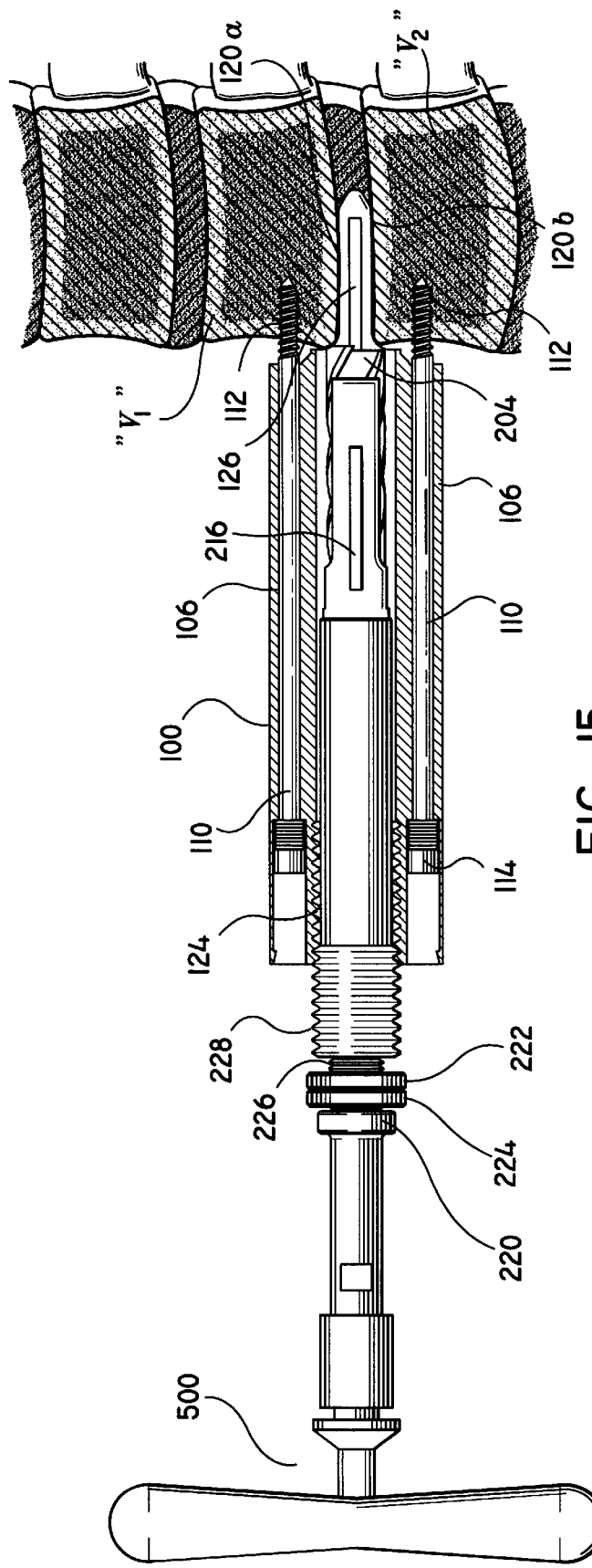
FIG. 15 is a view similar to the view of FIG. 14 illustrating insertion of the drilling instrument into the surgical retractor.
Figure 16:
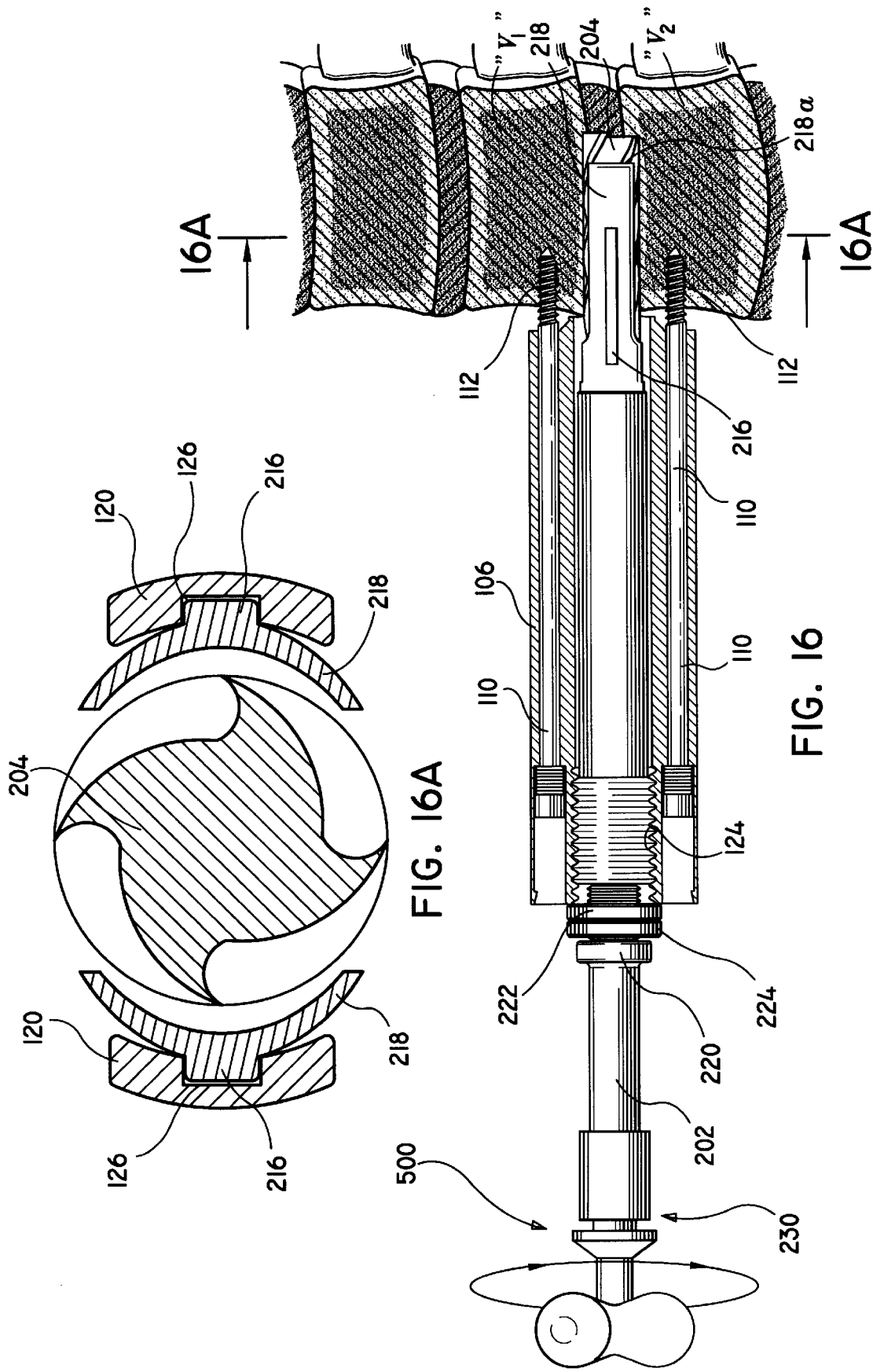
FIG. 16 is a view similar to the view of FIG. 15 illustrating advancement of the drilling instrument to drill a bore within adjacent vertebrae.

Referring now to FIG. 15, the drilling instrument 200 is now utilized to prepare the disc space and vertebral end plates for insertion of the fusion implant. The cutting depth of drilling instrument 200 is adjusted as desired (i.e., to correspond to the length of the fusion implant) by adjusting collars 222, 224 of the drilling instrument 200. In particular, collar 222 is moved to the desired position on threaded portion 226 on the drill shaft 202 and locking collar 224 is moved adjacent the collar 222 to lock the collar 222 at the position. With the T-handle 500 mounted to drilling instrument 200, by corresponding reception of hex-head mounting structure 230 within hex-head bore 502 of handle 500, the instrument is introduced into retractor sleeve 102. Preferably, drill instrument 200 is inserted within retractor sleeve 102 whereby axial splines 216 on the exterior surface of extension sleeve 206 are received within internal recesses 126 extending the length of the retractor sleeve 102 and retractor arms 120. T-shaped handle 500 is thereafter rotated which causes drill shaft 202 and drill bit 204 to rotate. With reference to FIGS. 16 and 16A, as drill shaft 202 rotates, it also advances within retractor sleeve 102 due to the threaded engagement of threaded portion 228 on the drill shaft 202 with internal threaded portion 124 of retractor sleeve 102 thereby advancing the drill bit 204 into the adjacent vertebrae "$v_1$, $v_2$" to form a circular bore in the end plates of the adjacent vertebrae. In addition, as drill shaft 202 advances it also drives extension sleeve 206 distally within the adjacent vertebrae. Due to the interengagement of axial splines 216 and longitudinal recesses 126, extension sleeve 206 advances without rotating whereby cutting surfaces 218a at the distal end of extension sleeve 206 cuts through a shearing action into the adjacent vertebrae "$v_1$, $v_2$". Thus, the cutting surfaces 218a of the cutting arms 218 are retained at the desired angular orientation adjacent retractor arms 120. The arcuate orientation of the cutting surfaces 218a of extension sleeve 206 in combination with drill bit 204 form a general elliptical opening in the adjacent vertebrae "$v_1$, $v_2$". It is to be noted that drilling instrument is advanced within retractor sleeve 102 until positioning collar 222 engages the proximal end of the retractor sleeve as shown in FIG. 16—the length of travel of drilling instrument being predetermined by adjusting collars 222, 224 as discussed above.

Subsequent to the drilling process, fusion implant 300 is packed with bone growth inducing substances as is conventional in the art and end cap 312 is threaded into a threaded recess of implant body 302. The fusion implant 300 is then mounted on insertion instrument 400 by cooperative engagement of the engaging structure 402 of the insertion instrument with the implant 300. Details of the mounting of implant 300 to insertion instrument 400 may be ascertained by reference to the '120 application.

Figure 17:
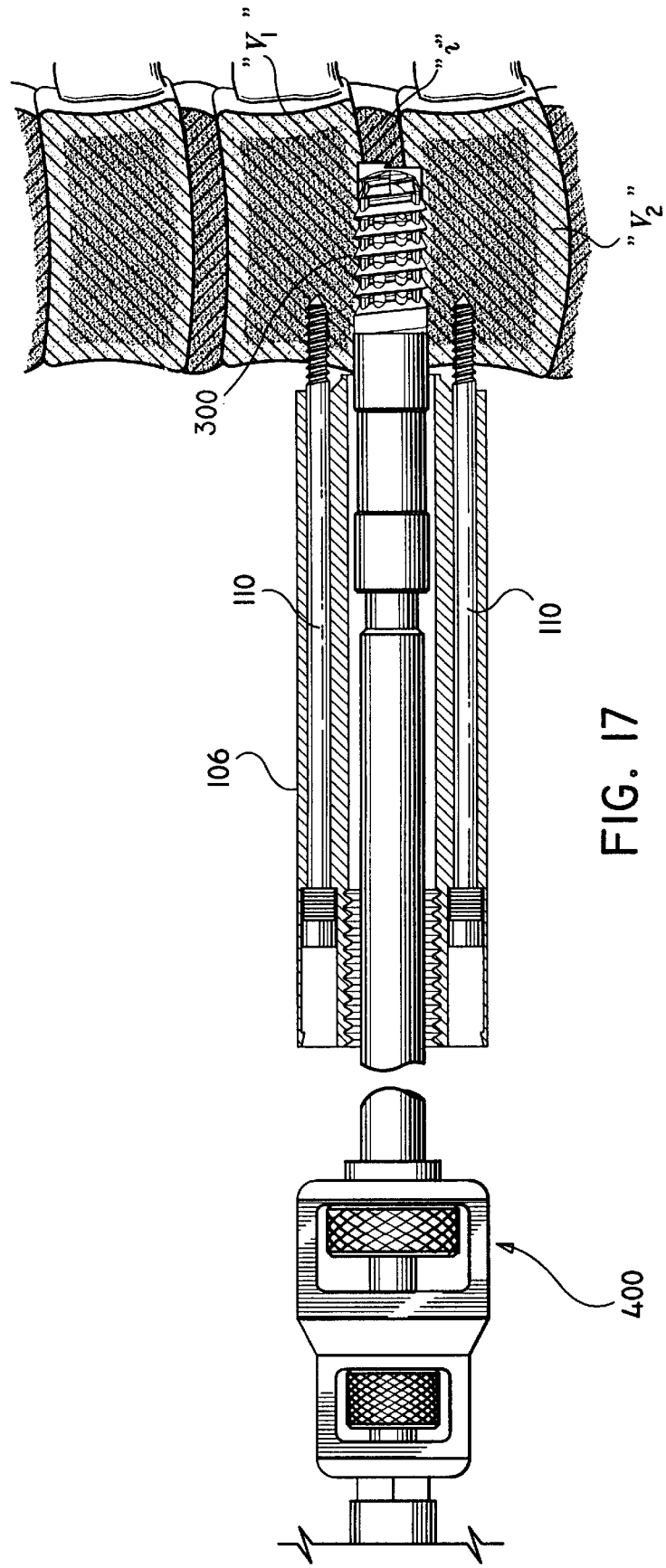
FIG. 17 is a view similar to the view of FIG. 16 illustrating insertion of the insertion instrument and mounted fusion implant into the surgical retractor to insert the implant.

Referring now to FIG. 17, insertion instrument 400 and mounted implant 300 is introduced within retractor 100 and advanced to a position adjacent the vertebral bodies "$v_1$, $v_2$". Thereafter, insertion instrument 400 is rotated via T-shaped handle 500 which is mounted to the instrument 400 to thereby cause corresponding rotation of fusion implant 300. As fusion implant 300 rotates, the thread 308 of the implant body 302 bites into the vertebral bodes "$v_1$, $v_2$". Continued rotation of insertion tool 400 causes implant 300 to be self-tapped within the preformed bore implant 300 is released from its mounting to insertion tool 400 and the instrument 400 and retractor 100 are removed from the disc area.

Figure 18:
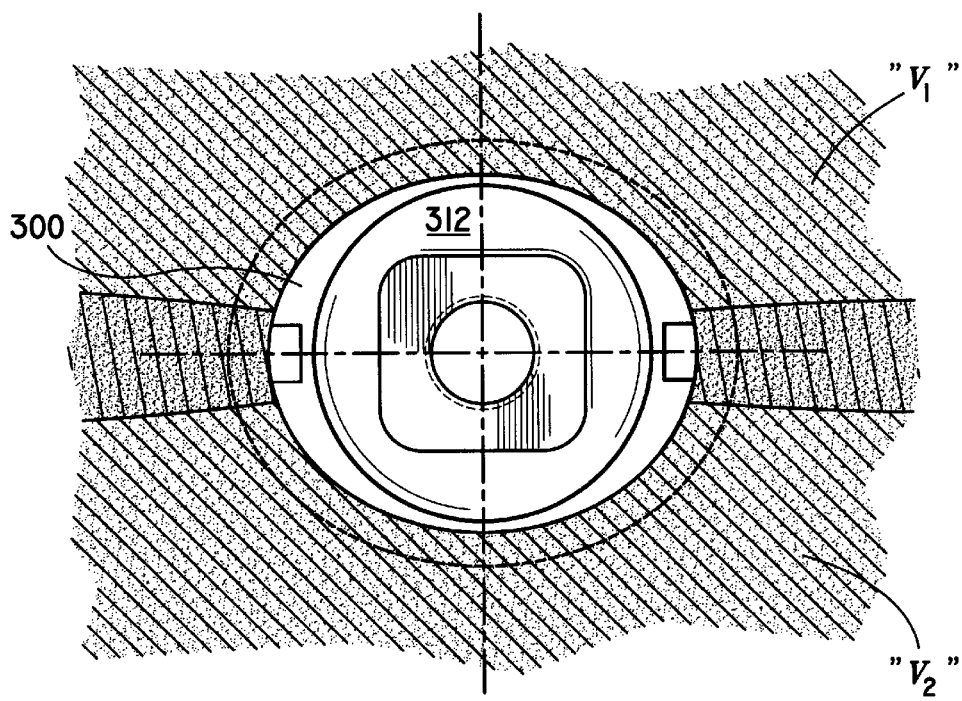
FIG. 18 is a sectional view illustrating the fusion implant mounted within the intervertebral space.
Figure 19:
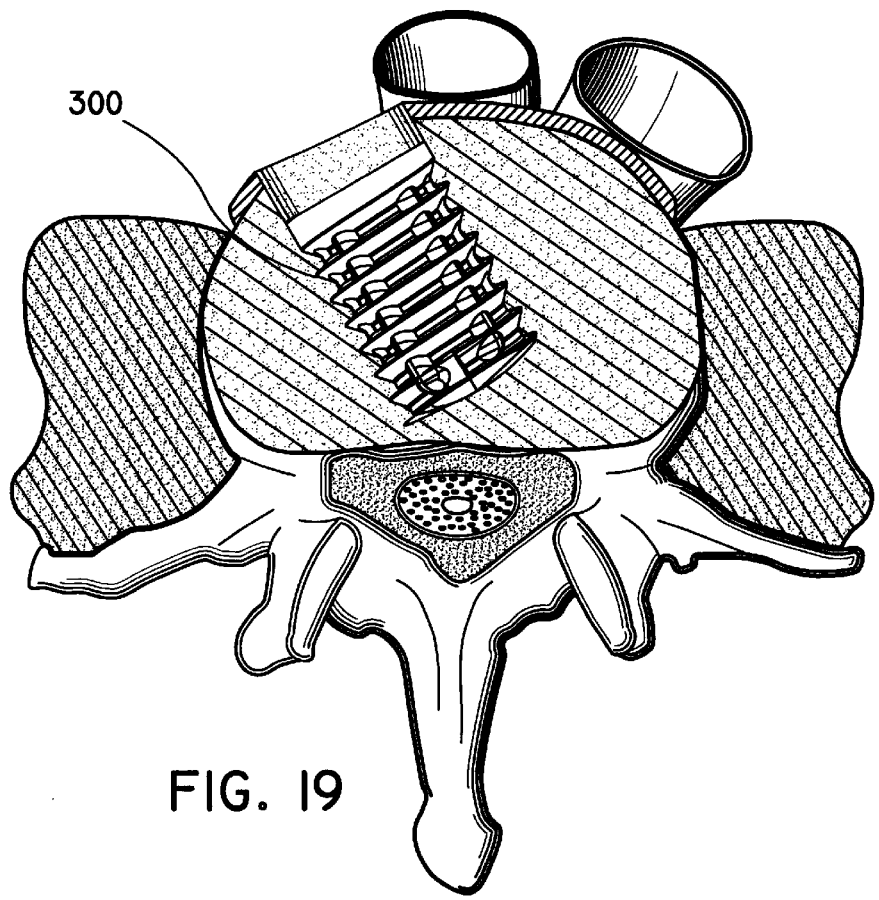
FIG. 19 is a view further illustrating the fusion implant mounted within the intervertebral space.

FIGS. 18–19 depict fusion implant 300 inserted within the intervertebral space "i". As shown, fusion implant 300 forms a strut across the intervertebral space "i" to maintain the adjacent vertebrae "$v_1$, $v_2$" in appropriate spaced relation during the fusion process. The implant is thus preferably inserted at an angle of between about 15 degrees and about 45 degrees, and more preferably at about 30 degrees to the longitudinal axis of the spine and to the right of the great vessels as view anteriorly. As also shown, in the inserted position of implant 300, the major axis "a" is in general parallel relation to the vertebral end plates thus presenting the great arc or surface area of implant body 302 to contact and support the adjacent vertebrae. Over a period of time, the adjacent vertebral tissue communicates through apertures 310 with the bone growth inducing substances within the interior cavity of implant 300 to form a solid fusion. Thus only one implant is required.

While the above description contains many specifics, these specifics should not be construed as limitations on the scope of the disclosure, but merely as exemplifications of preferred embodiments therefor. Those skilled in the art will envision many other possible variations that are within the scope and spirit of the disclosure as defined by the claims appended hereto.

What is claimed is:

1. A system for drilling a bore in adjacent vertebrae to facilitate the insertion of a fusion implant, which comprises:

a surgical retractor including a sleeve member having proximal and distal end portions and defining a longitudinal opening, the distal end portion configured for insertion at least partially into an intervertebral space between adjacent opposed vertebrae to distract the adjacent vertebrae; and a drill instrument positionable within the longitudinal opening of the surgical retractor, the drill instrument including:

an elongate member defining at least one distal cutting surface; and a drill member disposed within the elongate member and having a distal cutting head, the drill member being rotatably movable within the elongate member and being longitudinally fixed to the elongate member such that advancement of the drill member within the adjacent vertebrae causes corresponding advancement of the elongate member such that the distal cutting surface and the distal cutting head cooperate to cut a bore in the adjacent vertebrae.

2. The system according to claim 1 wherein the distal end portion of the sleeve member of the surgical retractor includes two spaced apart retractor arms having first and second supporting surfaces.

3. The system according to claim 2 wherein the elongate member of the drill instrument includes first and second diametrically opposed distal cutting surfaces.

4. The system according to claim 1 including alignment means for aligning and maintaining the elongate member of the drill instrument at a predetermined angular orientation within the sleeve member of the surgical retractor.

5. The system according to claim 4 wherein the alignment means includes at least one groove defined in the sleeve member of the surgical retractor, the at least one groove dimensioned to accommodate a corresponding spline of the elongate member.

6. The system according to claim 1 wherein the sleeve member of the surgical retractor includes an internal threaded portion, the internal threaded portion threadably engageable with an external threaded portion of the drill instrument whereby rotation of the drill instrument causes distal translation of the drill instrument relative to the surgical retractor.

7. The system according to claim 1 including at least one anchoring member associated with the elongate member and moveable relative to the elongated member to facilitate mounting to vertebrae.

8. The system according to claim 1 wherein the longitudinal opening of the sleeve member of the surgical retractor extends substantially the length of the sleeve member.

9. A system for drilling a bore in adjacent vertebrae to facilitate the insertion of a fusion implant, which comprises:

a surgical retractor including a sleeve member having proximal and distal end portions and defining a longitudinal opening, the distal end portion configured for insertion at least partially into an intervertebral space between adjacent opposed vertebrae to distract the adjacent vertebrae, the sleeve member including an internal threaded portion;

a drill instrument positionable within the longitudinal opening of the surgical retractor, the drill instrument including a drill member having a distal cutting head and an external threaded portion engageable with the internal threaded portion of the retractor whereby rotation of the drill instrument causes distal translation of the drill instrument relative to the surgical retractor.

10. The system according to claim 9 wherein the distal end portion of the sleeve member of the surgical retractor includes two spaced apart retractor arms having first and second supporting surfaces.

11. A method for performing a surgical procedure, comprising the steps of:

providing a surgical retractor including an elongate member having an outer wall and defining proximal and distal end portions, the elongate member having a longitudinal opening, the distal end portion including two spaced apart retractor arms having first and second supporting surfaces, the retractor arms being fixed with respect to the outer wall, and at least one anchor member mounted to the elongate member;

inserting the retractor arms within the intervertebral space whereby the fist and second supporting surfaces of each retractor arm respectively engage and distract the adjacent opposed vertebrae;

mounting the surgical retractor to the adjacent vertebrae by securing the at least one anchor member to the adjacent vertebrae; and performing the surgical procedure adjacent the distracted vertebrae.

12. A method for performing a surgical procedure, comprising the steps of:

providing a surgical retractor including an elongate member having proximal and distal end portions and defining a longitudinal opening, the distal end portion including two spaced apart retractor arms having first and second supporting surfaces, and at least one anchor member mounted to the elongate member;

inserting the retractor arms within the intervertebral space whereby the first and second supporting surfaces of each retractor arm respectively engage and distract the adjacent opposed vertebrae;

mounting the surgical retractor to the adjacent vertebrae by securing anchor members associated with the surgical retractor to the adjacent vertebrae; and introducing surgical instrumentation within the opening of the surgical retractor to perform the surgical procedure adjacent the distracted vertebrae.

13. A method for fusing adjacent vertebral bodies, comprising the steps of:

a) accessing the intervertebral disc space;

b) providing a retractor including a retractor sleeve having proximal and distal end portions, the distal end portion having opposed retractor arms extending in a general longitudinal direction;

c) positioning the retractor arms within the intervertebral disc space whereby first and second supporting surfaces of each arm contact opposed vertebra bodies;

d) introducing a drill instrument into the retractor sleeve and advancing the drill instrument within the sleeve to the disc space, the drill instrument including an elongate member defining at least one distal cutting surface and a drill member rotatably mounted within the elongate member and having a distal cutting head;

e) actuating the drill instrument such that the distal cutting head of the drill member and the distal cutting surface of the elongate member are advanced into the adjacent vertebrae to cooperate and cut a bore in the vertebra bodies;

f) removing the drill instrument from the sleeve; and g) introducing a fusion implant into the bore.

14. The method according to claim 13 wherein the bore formed in the vertebral bodies defines a general elliptical cross-sectional dimension and wherein the step of introducing includes inserting a fusion implant having a general elliptical cross-sectional dimension into the bore.

15. The method according to claim 14 wherein in a final inserted position of the fusion implant, a major axis of the implant is in the transverse direction generally parallel to the vertebral end plates.

16. A surgical retractor instrument comprising an elongated member defining an outer wall portion and having proximal and distal end portions, the elongated member defining a longitudinal passage for reception of a surgical instrument, the distal end portion having first and second retractor arms extending in a general longitudinal direction, the retractor arms being stationary with respect to the outer wall portion of the elongated member, each retractor arm having first and second supporting surfaces for engaging opposed tissue portions, each retractor arm defining a dimension between the first and second supporting surfaces sufficient to distract the opposed tissue portions upon insertion thereof, and at least one anchoring member mounted to the elongated member and moveable relative to the elongated member to facilitate mounting to the tissue portion.

17. The surgical retractor according to claim 16 wherein the first and second supporting surfaces of each retractor arm are in general parallel relation.

18. The surgical retractor according to claim 17 wherein each retractor arm has a tapered end portion for facilitating insertion within an intervertebral space.

19. The surgical retractor according to claim 17 wherein the first and second supporting surfaces of each retractor arm are in general parallel relation to a longitudinal axis of the elongated body.

20. The surgical retractor according to claim 16 wherein the longitudinal passage of the elongated member extends substantially the length of the elongated member.

21. A surgical retractor comprising an elongated member having proximal and distal end portions and defining a longitudinal passage for reception of a surgical instrument, the distal end portion having first and second retractor arms extending in a general longitudinal direction, each retractor arm having first and second supporting surfaces for engaging opposed tissue portions, each retractor arm defining a dimension between the first and second supporting surfaces sufficient to distract the opposed tissue portions upon insertion thereof, and at least one anchoring member mounted, to the elongated member and moveable relative to the elongated member to facilitate mounting to the tissue portion, the at least one anchoring member having a distal screw thread wherein rotation of the one anchoring member advances the screw thread into the tissue portion.

22. A surgical retractor comprising an elongated member having proximal and distal end portions and defining a longitudinal passage for reception of a surgical instrument, the distal end portion having first and second retractor arms extending in a general longitudinal direction, each retractor arm having first and second supporting surfaces for engaging opposed tissue portions, each retractor arm defining a dimension between the first and second supporting surfaces sufficient to distract the opposed tissue portions upon insertion thereof;

at least one anchoring member mounted to the elongated member and moveable relative to the elongated member to facilitate mounting to the tissue portion; and an outer rail extending longitudinally along an outer surface of the elongated member, the rail defining a longitudinal opening for at least partial reception of the at least one anchoring member.

23. The surgical retractor according to claim 22 including first and second anchoring members mounted to the elongated member.

24. The surgical retractor according to claim 23 including first and second diametrically opposed outer rails extending longitudinally along an outer surface of the elongated member, the first and second rails each defining a longitudinal opening for reception of respective first and second anchoring members.

25. A surgical drill instrument for drilling a bore in bony tissue comprising an elongate member defining a longitudinal axis and having a longitudinal passageway and a drill member positioned within the longitudinal passageway of the elongate member and mounted for rotational movement therein, the elongate member defining at least one distal cutting surface dimensioned to cut bony tissue, the drill member including a distal cutting head, the drill member operatively connected to the elongate member such that rotation and advancement of the drill member causes corresponding advancement of the elongate member such that the one distal cutting head surface of the elongate member and the distal cutting head of the drill head cooperate to form a substantially elliptical bore in the bony tissue upon advancement therein.

26. The surgical retractor according to claim 25 wherein the elongate member includes first and second diametrically opposed distal cutting surfaces.

27. The surgical retractor according to claim 26 wherein the distal cutting surfaces are arcuately shaped.

28. A method for performing a surgical procedure, comprising the steps of:

providing a surgical retractor including an elongate member having proximal and distal end portions and defining a longitudinal opening extending along at least a portion of the length of the elongate member, the distal end portion including two spaced apart retractor arms having first and second supporting surfaces, the retractor arms being longitudinally fixed with respect to the proximal end portion of the elongate member;

inserting the retractor arms within the intervertebral space whereby the first and second supporting surfaces of each retractor arm respectively engage and distract the adjacent opposed vertebrae;

mounting the surgical retractor to the adjacent vertebrae by securing anchor members associated with the surgical retractor to the adjacent vertebrae; and introducing surgical instrumentation within the opening of the surgical retractor to perform the surgical procedure adjacent the distracted vertebrae.

* * * * *